United States Patent
Griffiths et al.

(10) Patent No.: US 6,348,423 B1
(45) Date of Patent: *Feb. 19, 2002

(54) MULTILAYERED WOUND DRESSING

(75) Inventors: Bryan Griffiths; Elizabeth Jacques, both of Chester; Stephen Bishop, Flintshire, all of (GB)

(73) Assignee: Bristol-Myers Squibb Company, New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,321
(22) PCT Filed: Sep. 5, 1997
(86) PCT No.: PCT/EP97/04926
§ 371 Date: May 11, 1999
§ 102(e) Date: May 11, 1999
(87) PCT Pub. No.: WO98/09589
PCT Pub. Date: Mar. 12, 1998

(30) Foreign Application Priority Data

Sep. 5, 1996 (GB) .............................. 9618564

(51) Int. Cl.[7] ....................... B32B 27/04; B32B 27/12
(52) U.S. Cl. ..................... 442/123; 442/76; 442/79; 442/96; 442/394; 428/317.9; 428/919; 604/42
(58) Field of Search .................. 442/76, 79, 96, 442/123, 394; 428/312.7, 919; 604/42, 46

(56) References Cited

U.S. PATENT DOCUMENTS

| 3,868,955 | A | * | 3/1975 | Steiger et al. | 128/296 |
|---|---|---|---|---|---|
| 4,461,099 | A | * | 7/1984 | Bailly | 36/44 |
| 4,539,982 | A | * | 9/1985 | Bailly | 128/156 |
| 5,306,487 | A | * | 4/1994 | Karapasha et al. | 424/76.6 |
| 5,470,576 | A | * | 11/1995 | Patel | 424/445 |
| 5,925,009 | A | * | 7/1999 | Mahoney et al. | 602/44 |
| 5,973,221 | A | * | 10/1999 | Collyer et al. | 602/46 |

FOREIGN PATENT DOCUMENTS

| EP | 0 026 572 A1 | * | 6/1982 | A61L/13/02 |
|---|---|---|---|---|
| EP | 0 053 936 A2 | * | 6/1982 | A61L/15/03 |
| GB | 2 290 031 A | * | 12/1995 | A61L/13/02 |
| WO | WO 96/01658 | * | 1/1996 | A61L/15/18 |

* cited by examiner

Primary Examiner—Blaine Copenheaver
Assistant Examiner—Arti R. Singh
(74) Attorney, Agent, or Firm—Theodore R. Furman, Jr.; John M. Kilcoyne

(57) ABSTRACT

A novel wound dressing includes a fibrous absorbent layer for absorbing wound exudate, an odor layer for absorbing odor and a barrier layer interposed the fibrous absorbent and barrier layers. Preferably the barrier layer is vacuum perforated and the fibrous absorbent layer is of highly absorbent fibres capable of absorbing 25 grams of exudate per gram of dressing.

9 Claims, 2 Drawing Sheets

MULTILAYERED WOUND DRESSING

The present invention relates to a multi layered wound dressing particularly, but not exclusively, for use as a dressing on infected wounds and especially malodorous wounds such as infected ulcers.

Alginate fabrics have, in conjunction with charcoal cloth been used in wound dressings for malodorous wounds and examples of such commercially available dressings are sold under the trade marks KALTOCARB, ACTISORB PLUS and LYOFOAM C. A dressing available under the trade mark KALTOCARB comprises a non-woven alginate pad and charcoal cloth fused together with a polyamide net; a dressing available under the trade mark ACTISORB PLUS comprises charcoal cloth together with silver sealed within a nylon sleeve and may further include one or more absorbent layers; a dressing available under the trade mark LYOFOAM C includes viscose fibres treated with activated charcoal encapsulated by a layer of polyurethane foam.

EP 0099758 describes a composite wound dressing which can include alginate fabric used in conjunction with charcoal cloth. This wound dressing comprises a semipermeable membrane, which may comprise alginate, a supporting layer such as charcoal cloth and a biodegradable tissue interface such as sodium-calcium alginate. The supporting layer is located between the semi-permeable membrane and the biodegradable tissue interface.

GB 2228682 and GB 2290031 describe wound dressings which may include and odour adsorbing layer and have as their absorbent layer a layer or layers of foam. Neither document discloses the use of a fibrous absorbent layer in combination with an odour adsorbing layer.

EP 0026572 concerns a multilayered wound dressing which includes a layer of curative and absorbent material comprising a blend of one or more water soluble or swellable hydrocolloids and a binder which layer contacts the wound, an intermediate layer of deodorising material and an air and gas permeable layer which secures the dressing to the body. The curative and absorbent material is a homogeneous cohesive mass which is punched with holes so as not to impede the passage of gas away from the wound. A liquid impermeable material such as a non-woven fabric may be included in the dressing between the wound contacting layer and the deodorising layer.

A problem associated with known multi-layered dressings which employ charcoal cloth is that the dressing is a relatively rigid structure. This is a disadvantage since malodorous wounds tend to be sited in areas such as the neck or underarm where a highly conformable dressing is needed. In addition the wound contact layer tends to be somewhat hard which can cause discomfort to the patient especially when the dressing is changed.

Furthermore, malodorous wounds tend to be wounds that generate high levels of exudate. This leads not only to the problem of leakage of wound exudate but also, it is believed, limits the ability of the charcoal to adsorb malodours due to saturation.

We have now developed a multi layered wound dressing which alleviates the above problems and there is provided by the present invention a multi layered dressing comprising a
fibrous absorbent layer for absorbing wound exudate, a barrier layer and an odour adsorbing layer where said barrier layer is located between the absorbent layer and the odour adsorbing layer.

In use the dressing may be oriented so that the absorbent layer is closest to the wound and preferably so that the absorbent layer contacts the wound and surrounding skin.

The absorbent layer is fibrous and can comprise any biodegradable fibre. Preferred fibres for use in the absorbent layer of the present invention include those of alginate, viscose, modified cellulose, cellulose, polyester, polypropylene and co-polymers thereof, pectin, chitosan fibres, hyaluronic acid fibres or other polysaccharide fibres or fibres derived from gums. Most preferred are highly absorbent fibres such as OASIS™ fibre as disclosed in EP 0269393 A, modified cellulose fibres as described in WO93/12275 to Courtaulds Plc or GB9301258 to Courtaulds Plc and alginate fibres as described in WO 94/17227 to E. R. Squibb and Sons. By "highly absorbent" with-respect to the fibre it is meant that they can absorb at least 25 g/g of deionized water. Most aptly the fibres can absorb at least 60 times, more aptly at least 80 times, for example 80–280 times of their own weight, more aptly 90 to 150 times for example about 120 times of their own weight of deionized water. The fibres for use in the absorbent layer may also be mixed or blended to form a composite layer or may be fibres made of a mixture of any of the above ingredients.

The barrier layer deters the movement of exudate to the odour adsorbing layer while permitting the movement of odour to the odour adsorbing layer. The delay in the movement of exudate imposed by the barrier layer increases the time over which the dressing is able to adsorb odour and increases the quantity of odour adsorbed. The barrier can be of the type known as "one way wicking". This type of material is vacuum perforated over a small cone or micro funnel such that a small hole is formed which allows the movement of odours but deters the movement of exudate away from the absorbent layer. A preferred example is FLEXIFILM, an ethylene vinyl acetate film of the type sold by Tredegar. These films can be made from a range of polymers, for example high density polyethylene, polypropylene, medium density polyethylene, ethylene methyl acetate and ethylene vinyl acetate. Preferred is a film made from 50% EMA, 43% EVA and balance white colourant.

Alternatively the barrier layer can be a non-woven cloth that is impermeable to liquids but gas permeable. It is believed that the advantage of retaining the exudate in the absorbent layer and detering it from moving immediately into the odour adsorbing layer is that the maximum free surface area for odour adsorption is retained and therefore the dressing maintains its odour adsorbing properties for longer.

The odour adsorbing layer is preferably a charcoal cloth such as that manufactured by The Charcoal Cloth Company at 120 gsm. The odour adsorbing layer may also be charcoal coated material such as that made by Lantor.

Preferred embodiments of the present invention will now be described by way of example with reference to the accompanying drawings, in which.

Figure 1:
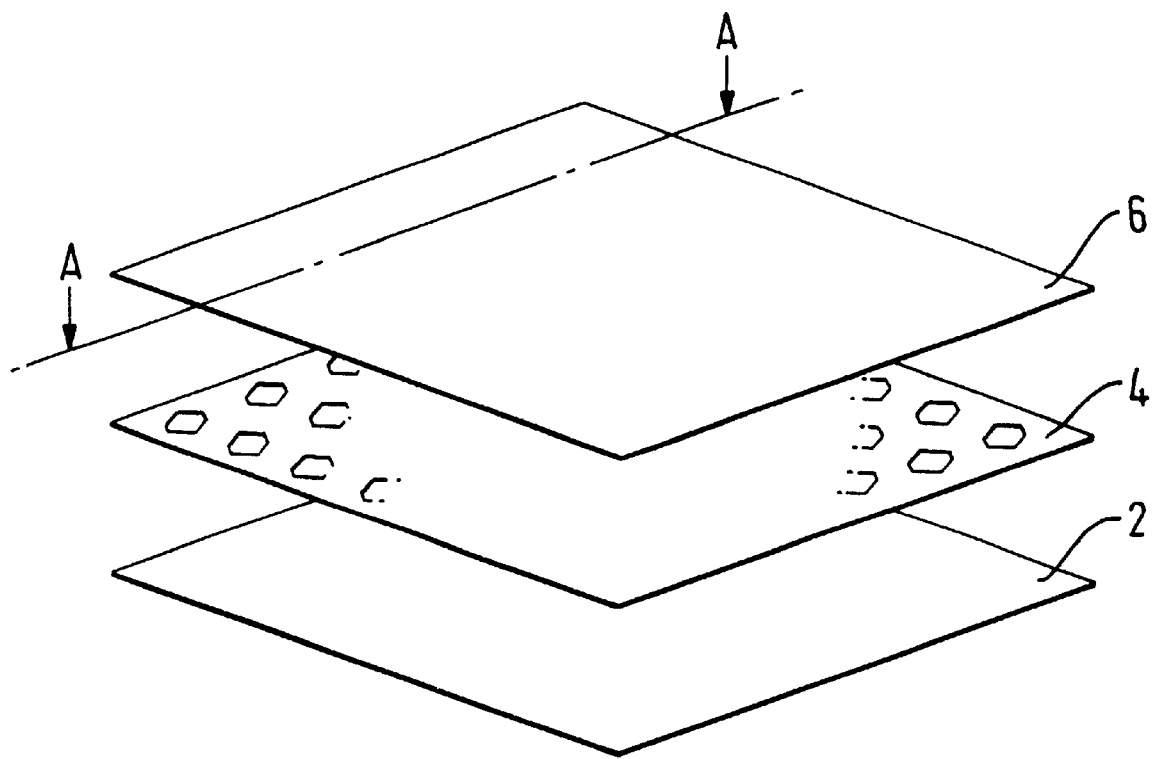
FIG. 1 is a schematic diagram of a multi layered wound dressing according to the invention.
Figure 2:
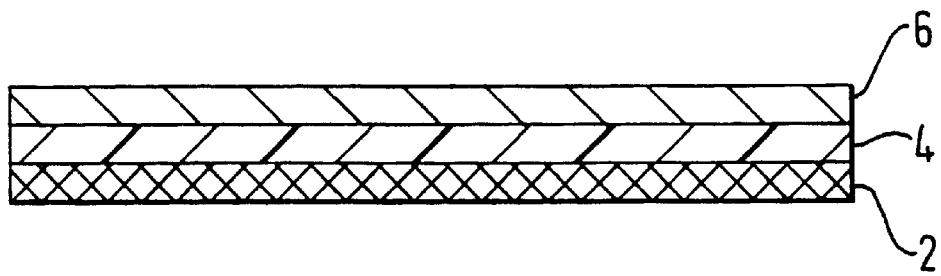
FIG. 2 shows a cross section of the dressing of FIG. 1 taken along the line A—A.

Referring now to FIG. 1 of the drawings the multi layered dressing comprises an absorbent layer (2), a barrier layer (4) and an odour adsorbing layer (6). The absorbent layer is made from a 70/30 blend of calcium/sodium alginate fibres of the type described in EP 43354 or EP 476756 to CV Laboratories Ltd and sold as a fibrous dressing in the product KALTOSTAT ex ConvaTec and cellulose fibres of the type described in WO93/12275 to Courtaulds and sold as a fibrous dressing in the product AQUACEL ex ConvaTec. The barrier layer is an ethylene vinyl acetate film with one-way wicking oriented to prevent the movement of exudate away from the wound (FLEXIFILM ex Tredegar). The odour adsorbing layer is a charcoal cloth (ex Charcoal Cloth Company).

Figure 3:
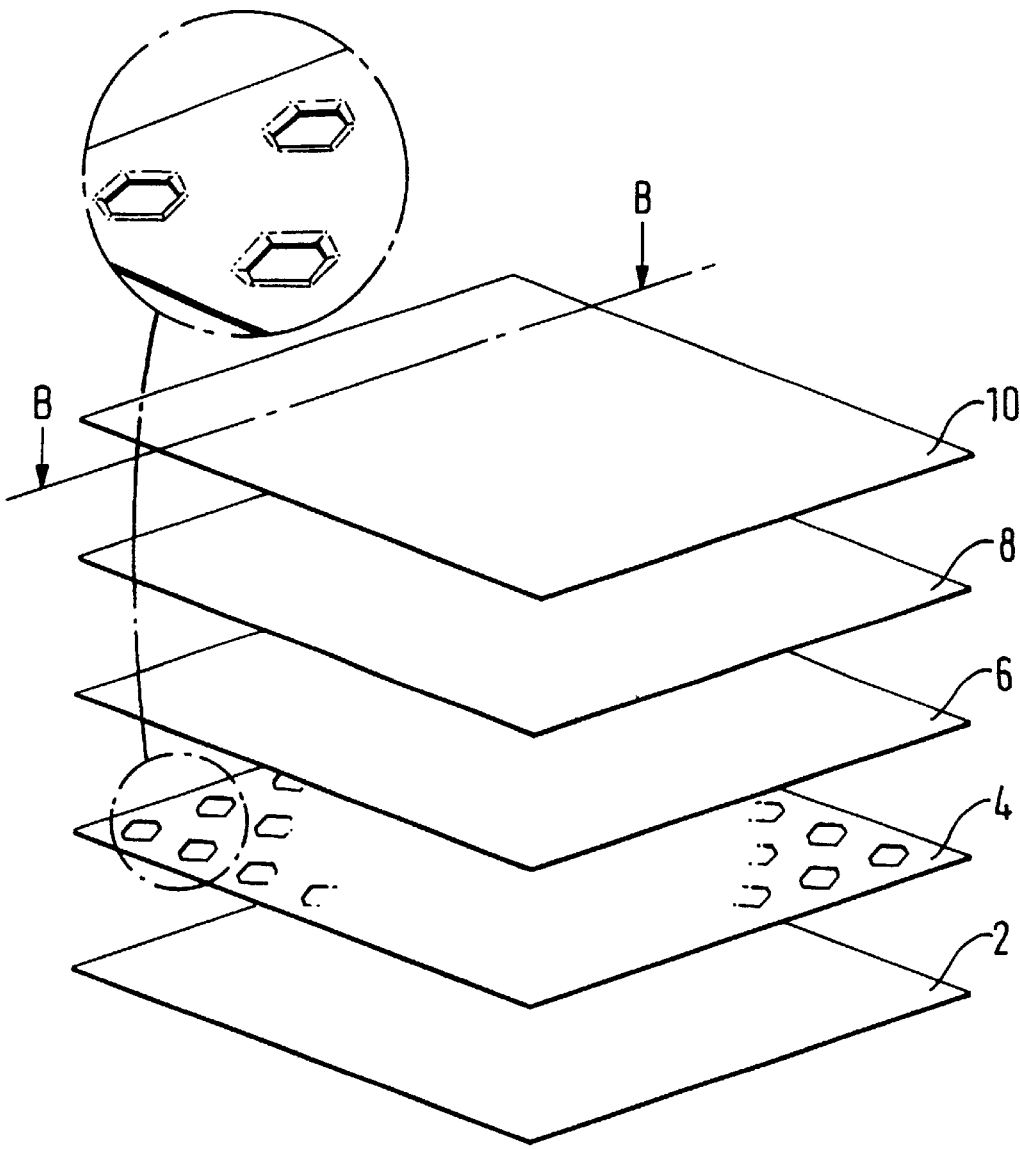
FIG. 3 is a schematic diagram of an alternative embodiment of the wound dressing according to the invention.
Figure 4:
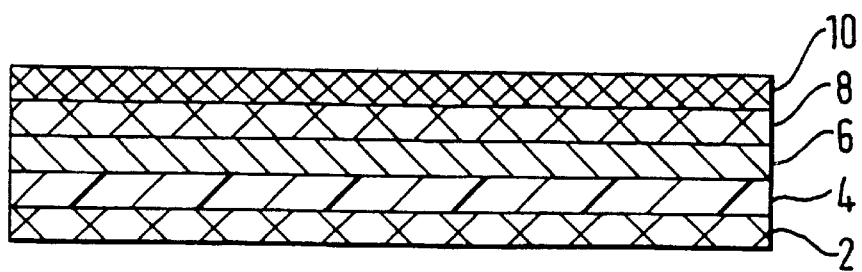
FIG. 4 is a cross section of the dressing of FIG. 3 taken on the line B—B.

FIG. 3 shows an alternative embodiment of the invention where the dressing comprises an absorbent layer (2) a barrier layer (4) and an odour adsorbing layer (6) as described for FIG. 1 along with a camouflage layer (8) made of a blend of DANAKLON ES-C-PHIL™ and viscose in a mix of 88.6% viscose and 11.4% Danaklon which provides cushioning and which prevents the blackness of the charcoal cloth being visible in the dressing, and a further barrier layer (10) which prevents strike through of exudate should the lower barrier layer (4) fail.

The dressing is placed on a wound, for example an ulcer, with the absorbent layer in contact with the wound.

Wound dressings in accordance with the present invention may be more absorbent, more conformable and provide a longer wear time than known dressings.

Preferred embodiments of the invention will now be illustrated in the following examples.

EXAMPLE 1

A multilayered dressing (Dressing A) according to the invention was made by placing the various layers as descibed for the embodiment of the invention shown in FIG. 3 on top of one another and heat sealing them together. A second dressing (Dressing B) was made in the same way as Dressing A except that the barrier layer was inverted. Samples measuring 10 cm×10 cm of both Dressings were then assessed in an accelerated test by placing the absorbent layer in contact with an absorbent material (LYOFOAM) which itself was in contact with a reservoir of Solution A (a solution of 142 mmol/L Na ions and 2.5 mmol/L of Ca ions)replenished at a flow rate of 30.4 ml/hr. A 2.72 Kg load was applied to each dressing to simulate pressure conditions in vivo. The time for exudate to strike through to the upper surface of the dressing and the fluid uptake of each of five samples of the dressings was then measured.

|  | Dressing A | Dressing B |
| --- | --- | --- |
| Time to strike through (mean/mins) | 11.904 | 1.646 |
| Fluid uptake (mean g/g) | 3.148 | 0.671 |

These results demonstrate the one-way wicking or "directionality" properties of the barrier layer. The greater fluid uptake of Dressing A shows the advantage of the effective use of the barrier layer on absorbtion.

EXAMPLE 2

The odour adsorbing properties of a dressing according to the invention were assessed by contacting Dressing A from Example 1, ACTISORB a commercially available dressing for use on malodourous wounds, and a control with a standard source of odour and subjectively evaluating the odour levels which permeate the dressings. This was done by taking a swab from a leg ulcer and growing the bacteria collected onto ceramic beads. One of the ceramic beads was then placed in a cooked meat broth to encourage further growth and the remainder of the beads saved to create further cultures. A standard volume of the broth was then placed in a jar (Payne Cup type) the opening of which was closed by a sample of Dressing A, ACTISORB or Dressing A without the odour adsorbing layer and each sample was also covered with a layer of OPSITE (a polyurethane film dressing coated with a layer of vinyl ether adhesive ex Smith and Nephew) on the side furthest from the broth to prevent escape of the broth during inversion of the jars. This was secured by an o-ring placed over the samples. A panel of between seven and eleven testers then sniffed each jar and subjectively awarded an odour level score between 0(low) and 5(high) for time zero ($T_0$). The jars were then inverted and the sniff test repeated every hour for five hours and at twenty four hours. The scores for each sample were then averaged. The test was repeated several days later.

| Time | Dressing A | ACTISORB PLUS | Control |
| --- | --- | --- | --- |
| $T_0$ | 1 | 1.1 | 2.2 |
| $T_1$ | 1.5 | 2.1 | 2.5 |
| $T_2$ | 1 | 3.1 | 2.7 |
| $T_3$ | 1.18 | 3 | 2.7 |
| $T_4$ | 1.3 | 3.3 | 3.2 |
| $T_5$ | 1.4 | 3.7 | 3.1 |
| $T_6$ | 1.7 | 3 | 4 |
| $T_0$ | 0.7 | 1.1 | 2.2 |
| $T_1$ | 2 | 2.4 | 3.6 |
| $T_2$ | 2.2 | 2.7 | 3.2 |
| $T_3$ | 1.7 | 2.9 | 2.9 |
| $T_4$ | 1.9 | 3.1 | 3.8 |
| $T_5$ | 1.9 | 3.1 | 3.8 |

These results show that Dressing A according to the invention consistently adsorbs more odour than either the control or a commercially available dressing designed for use with malodourous wounds.

EXAMPLE 3

An absorbent layer for use in dressings according to the invention was made by cutting fibres to a staple length of approximately 50 mm. The alginate fibres were of the type described in EP 43 354 or EP 476 756 to CV Laboratories Ltd and sold as a fibrous dressing in the product KALTOSTAT ex ConvaTec and the cellulose fibres were of the type described in WO93/12275 to Courtaulds and sold as a fibrous dressing in the product AQUACEL ex ConvaTec. The fibres were then separately weighed and crimped. The fibres were then fed into an opening machine in the ratio 70% alginate fibre-and 30% modified cellulose fibre to produce opened mixed fibre. The mixture was then fed to a hopper of a delivery device set to deliver the mixture to a carding machine so that it yielded carded web in the density range 70 to 240 gsm. From the carding machine the fibre web was taken and cross-lapped prior to being needle punched and rolled-up. The resulting product was a homogeneous blend of fibres that was soft to the touch and of good integrity.

What is claimed is:

1. A multi layered dressing comprising a fibrous absorbent layer for absorbing wound exudate, a barrier layer and an odour adsorbing layer where said barrier layer is located between the absorbent layer and the odour adsorbing layer, wherein the wound exudate absorbing component consists essentially of fiber.

2. A multi layered dressing as claimed in claim 1 wherein the barrier layer is substantially impermeable to liquids but is gas permeable.

3. A multi layered dressing as claimed in claim 1 wherein the barrier layer is a vacuum perforated film oriented to deter the movement of exudate to the odour adsorbing layer.

4. A multi layered dressing as claimed in claim 1 wherein the fibrous absorbent layer comprises biodegradable fibres.

5. A multilayered dressing as claimed in claim 4 wherein the fibrous absorbent layer comprises fibres selected from the group consisting of alginate, viscose, modified cellulose, cellulose, polyester, polypropylene, polypropylene copolymers, pectin, chitosan fibers, hyaluronic acid fibres, polysaccharide fibres and fibres derived from gums.

6. A multi layered dressing as claimed in claim 1 wherein the fibrous absorbent layer comprises highly absorbent fibres.

7. A multilayered dressing as claimed in claim 1 wherein said barrier layer is a vacuum perforated film.

8. A multi layered dressing as claimed in claim 1 wherein the fibrous absorbent layer comprises a blend of modified cellulose fibres with alginate fibres, said fibres having an absorbency of at least 25 g of water per g of fibre.

9. A method for the treatment of a wound comprising placing a multi layered dressing as claimed in claim 1 in direct contact with the wound.

* * * * *